US00PP34485P3

(12) United States Plant Patent
Ammerlaan

(10) Patent No.: US PP34,485 P3
(45) Date of Patent: Aug. 9, 2022

(54) ***ECHEVERIA* PLANT NAMED 'OVPEARLS09'**

(50) Latin Name: *Echeveria lilacina*
Varietal Denomination: OVPEARLS09

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 17/300,813

(22) Filed: Nov. 12, 2021

(65) Prior Publication Data

US 2022/0159889 P1 May 19, 2022

(30) Foreign Application Priority Data

Nov. 13, 2020 (QZ) ..... PBR 2020/2875

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373, 226, 263.1
CPC ... A01H 5/12; A01H 5/00; A01H 5/02; A01H 6/32; A01H 6/00; A01H 1/107
See application file for complete search history.

*Primary Examiner* — June Hwu
(74) *Attorney, Agent, or Firm* — Samuel R. McCoy, Jr.

(57) ABSTRACT

A new and distinct variety of *Echeveria* plant named 'OVPEARLS09' which is characterized by a flattened profile with foliage that is loosely held in a basal rosette, narrowly obovate to broad spathulate foliage with a conspicuous globular growth on the abaxial surface, glaucous foliage that is covered with a layer of greyed-green epicuticular wax which gives the foliage a pale greyed-green appearance, juvenile foliage that is lightly suffused with greyed-purple along the distal portion of the margins and apex, and lightly undulated foliar margins. The new variety has shown to be uniform and stable in the resulting generations from asexual propagation.

3 Drawing Sheets

Latin name of the genus and species: The Latin name of the genus and species of the novel variety disclosed herein is *Echeveria lilacina.*

Variety denomination: The inventive variety of *Echeveria* disclosed herein has been given the variety denomination 'OVPEARLS09'.

This application claims priority to the Community Plant Variety Rights application number 2020/2875, filed on Nov. 13, 2020, which is herein incorporated by reference.

BACKGROUND OF THE INVENTION

Parentage: 'OVPEARLS09' is a naturally-occurring, whole-plant mutation of an unnamed *Echeveria lilacina* plant (not patented) which was discovered by the inventor in the summer of 2016 at a commercial greenhouse in Bleiswijk, the Netherlands. The mutation was noted for its light greyed-green, glaucous foliage with conspicuously undulating margins.

Asexual Reproduction: Asexual reproduction of the new cultivar 'OVPEARLS09', by way of rooting leaf cuttings, was first initiated in Summer of 2016 at the inventor's commercial greenhouse. in Bleiswijk, the Netherlands. Through four subsequent generations, the unique features of this cultivar have proven to be stable and true to type.

SUMMARY OF THE INVENTION

The cultivar 'OVPEARLS09' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS09'. These characteristics in combination distinguish 'OVPEARLS09' as a new and distinct *Echeveria* cultivar:

1. 'OVPEARLS09' exhibits a flattened profile with succulent foliage that is loosely held in a non-branched basal rosette; and
2. 'OVPEARLS09' exhibits narrowly obovate to broad spathulate foliage with a conspicuous globular growth on the abaxial surface; and
3. 'OVPEARLS09' exhibits greyed-green, glaucous foliage that is covered with a layer of greyed-green epicuticular wax which gives the foliage a pale greyed-green appearance; and
4. 'OVPEARLS09' exhibits juvenile foliar margins that are lightly suffused with greyed-purple along the distal margins and apex; and
5. 'OVPEARLS09' exhibits foliar margins that are lightly undulated.

BOTANICAL DESCRIPTION OF THE PLANT

Figure 1:
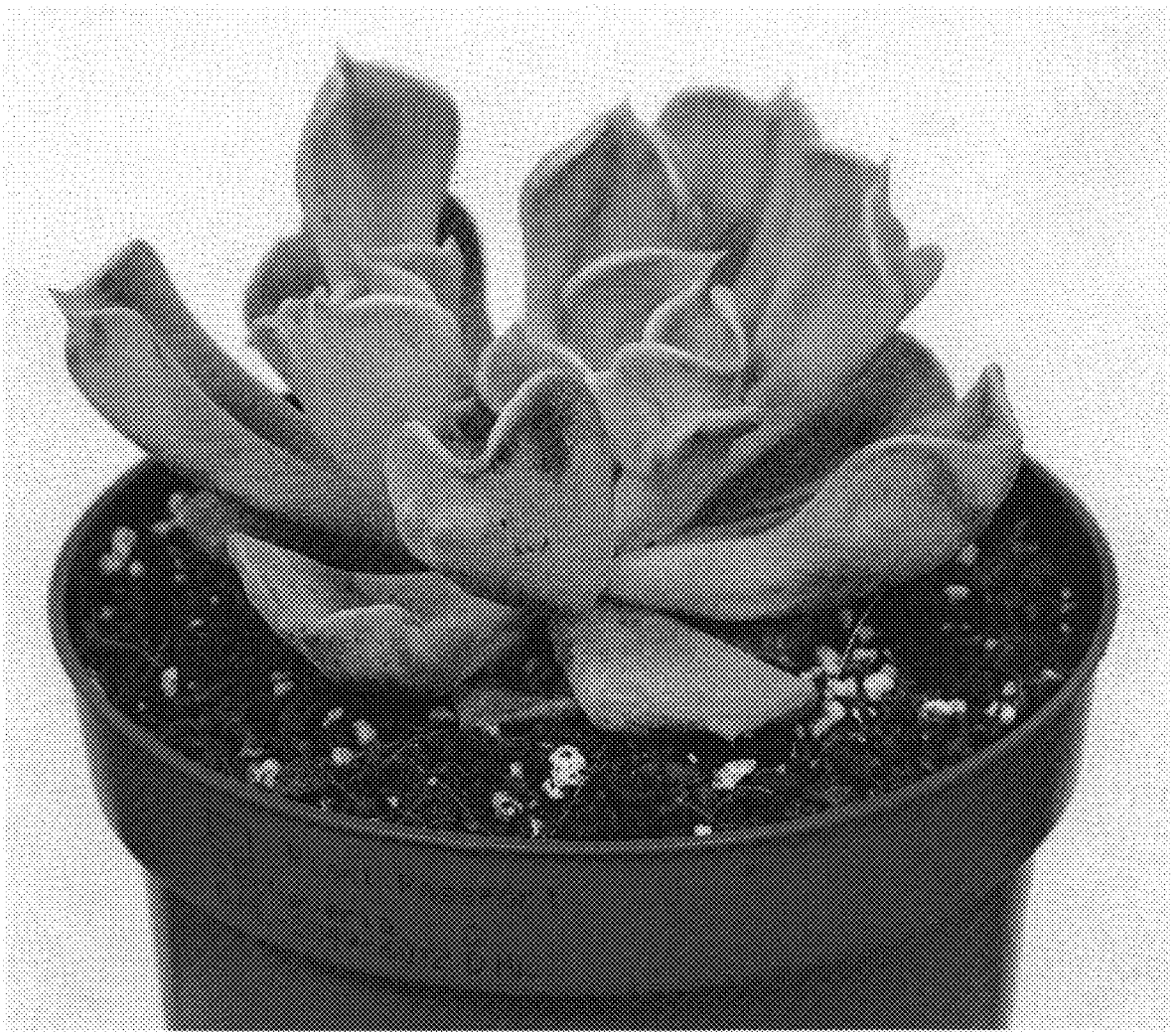
FIG. 1 illustrates, as nearly true as it is reasonably possible to make the same in color photographs of this type, an exemplary plant of 'OVPEARLS09' grown in a commercial greenhouse in Bleiswijk, the Netherlands. This plant is approximately 1 year old, shown planted in a 10 cm container.
Figure 2:
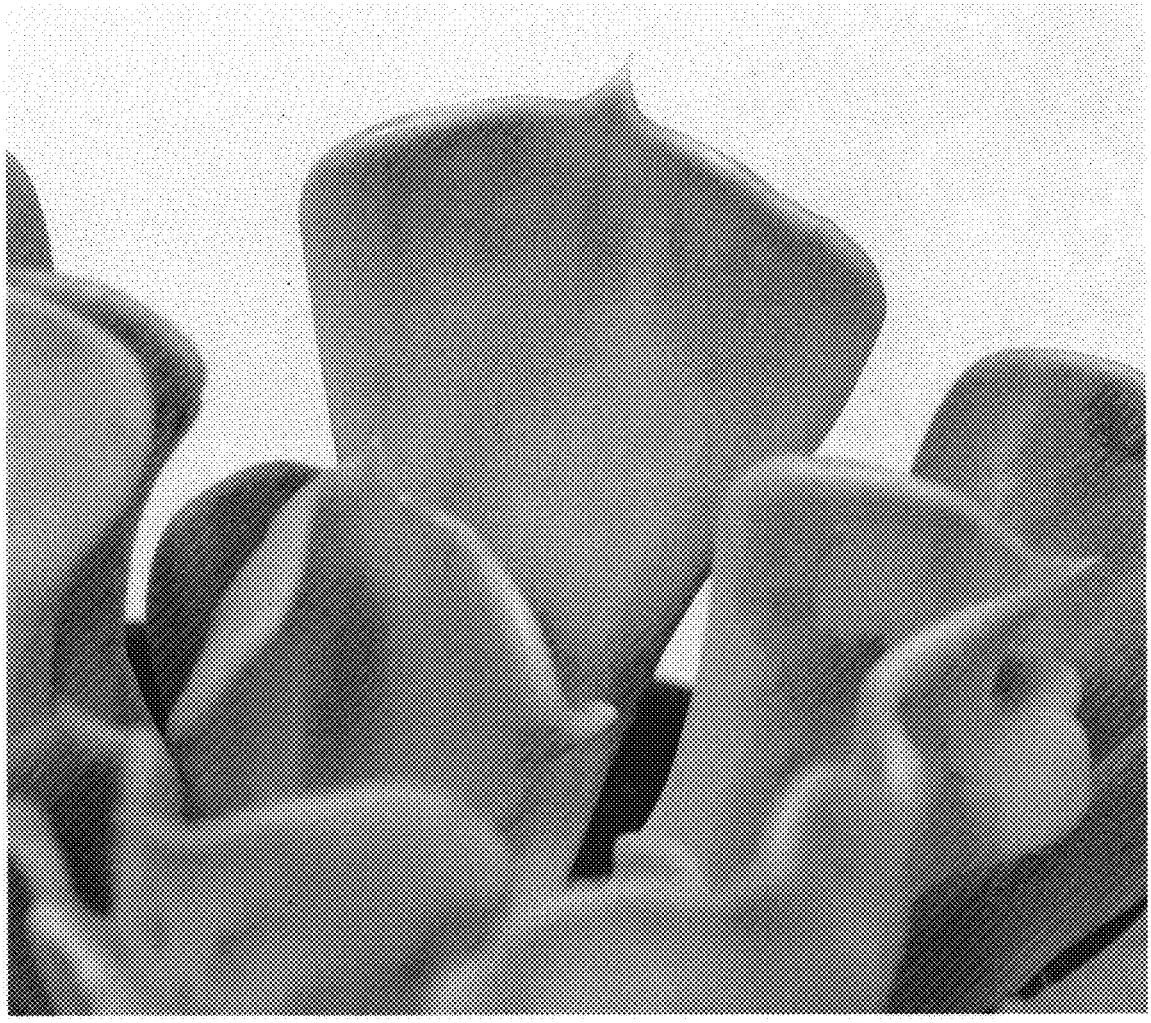
FIG. 2 illustrates, as nearly true as it is reasonably possible to make the same in color photographs of this type, the adaxial surface of the mature foliage 'OVPEARLS09'.
Figure 3:
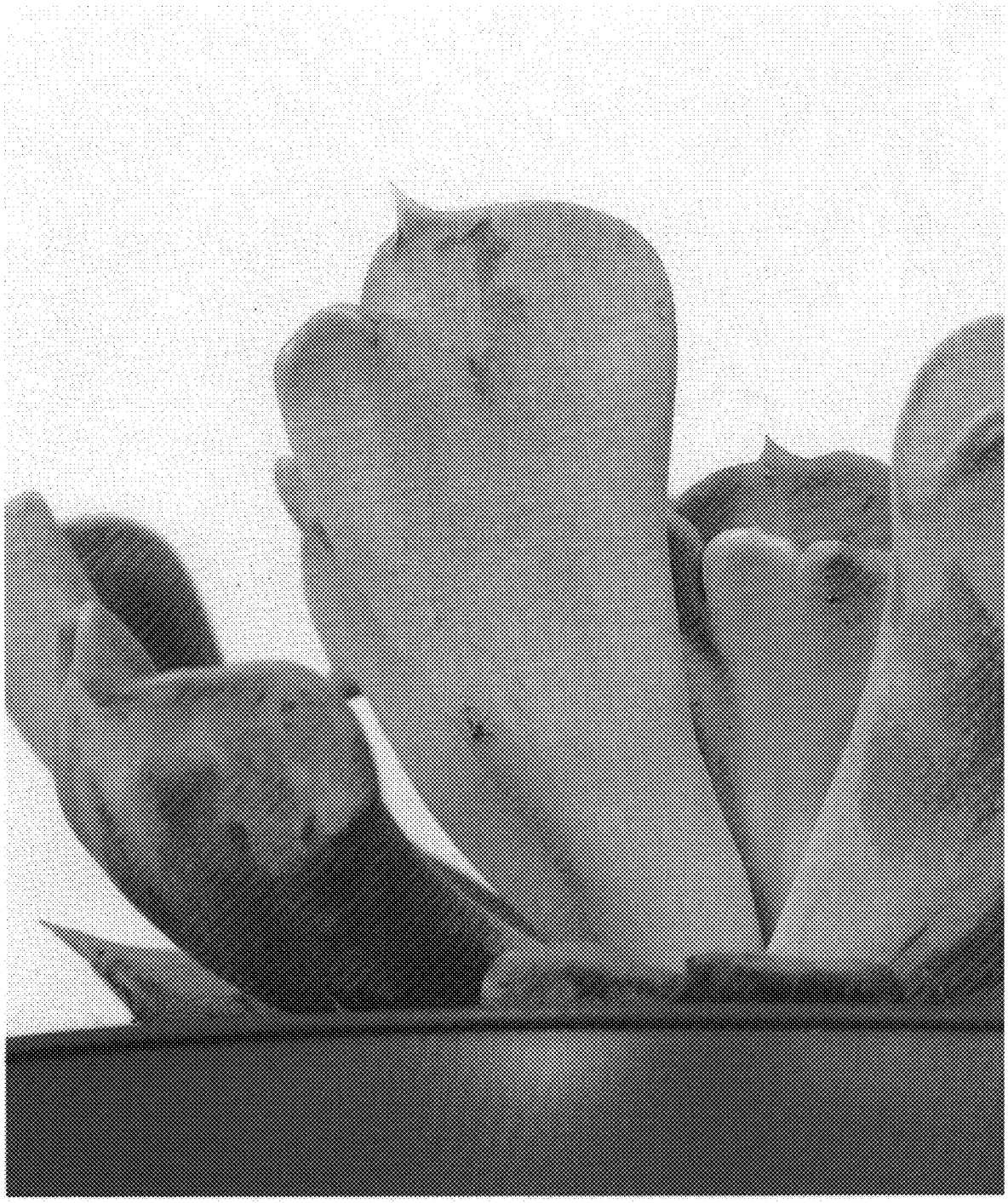
FIG. 3 illustrates, as nearly true as it is reasonably possible to make the same in color photographs of this type, the abaxial surface of the mature foliage 'OVPEARLS09'.

The following observations and measurements made in November of 2020 describe averages from a sample set of six specimens of 1 year old 'OVPEARLS09' plants grown in 10 cm nursery containers at commercial greenhouse in Bleiswijk, the Netherlands. Plants were produced using conventional greenhouse production protocols for *Echeveria* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS09' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVPEARLS09' and a comparison with the parent and closest known comparator is provided below.

Plant description:

*Growth habit*.—Succulent perennial with foliage growing in a compact, non-branched basal rosette.

*Plant form*.—Flattened.

*Height from soil level to top of foliar plane*.—5.9 cm.

*Plant spread*.—Average of 10.9 cm.

*Growth rate*.—Moderately fast.

*Plant vigor*.—Moderately vigorous.

*Propagation*.—Type — Leaf cuttings. Time to initiate rooting — Approximately 5 weeks at an approximate temperature of 21 degrees Celsius. Crop time — Approximately 1 year to produce a marketable plant in a 10 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—No stems or branches; leaves arranged in a basal rosette.

Foliage:

*Arrangement*.—Rosette.

*Division*.—Simple.

*Attachment*.—Sessile.

*Quantity*.—Approximately 23 leaves per rosette.

*Shape*.—Narrow obovate to broad spathulate. An irregularly globular growth is present on the abaxial surface of the foliage. Growths are 0.8 cm long and 0.9 cm wide, on average.

*Dimensions*.—6.0 cm long, 2.7 cm wide, and 0.7 cm thick, on average.

*Aspect*.—Concave.

*Attitude*.—Foliage is held upright and outward at and near the center of the rosette and becomes progressively more relaxed towards the outer whorls of foliage; mature foliage is 35 degrees from horizontal.

*Apex*.—Cuspidate.

*Base*.—Long cuneate.

*Margin*.—Entire; lightly undulated.

*Pubescence, texture and luster of the adaxial surface*.—Glabrous, smooth, and matte; moderately to strongly glaucous.

*Pubescence, texture and luster of the abaxial surface*.—Glabrous, smooth, and matte; moderately to strongly glaucous.

*Color*.—Juvenile foliage, adaxial surface — Greyed-green, nearest to a mixture of RHS 191A and 191B, and fading lighter towards the base, nearest to RHS 196D; margined with a lighter shade of greyed-green, nearest to in between RHS 192B and 192C; margins at and near the apex are lightly suffused with greyed-purple, nearest to RHS 186C. Leaves are covered with a thin layer of epicuticular wax which is colored greyed-green, nearest to RHS 188A. Juvenile foliage, abaxial surface — Greyed-green, nearest to RHS 191B, and fading lighter towards the base, nearest to RHS 196D; margined with a lighter shade of greyed-green, nearest to in between RHS 192B and 192C; margins at and near the apex are lightly suffused with greyed-purple, nearest to RHS 186C. Leaves are covered with a thin layer of epicuticular wax which is colored greyed-green, nearest to RHS 188A. Mature foliage, adaxial surface — Nearest to in between yellow-green and greyed-green, RHS 148A and 191A; fading lighter towards the base, nearest to a mixture of RHS 148C, 194C and 195B; distally margined and tipped with greyed-green, nearest to RHS 195B. Leaves are covered with a thin layer of epicuticular wax which is colored greyed-green, nearest to RHS 188A. Mature foliage, abaxial surface — Yellow-green, nearest to RHS 148B, and fading lighter towards the base, nearest to RHS 148C; distally margined and tipped with greyed-green, nearest to RHS 195B. Leaves are covered with a thin layer of epicuticular wax which is colored greyed-green, nearest to RHS 188A.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANT

Plants of the new cultivar 'OVPEARLS09' differ from the parent, an unnamed *Echeveria lilacina* plant (not patented) in the following characteristics described in Table 1 below.

TABLE 1

| Characteristic | 'OVPEARLS09' | The parent. |
|---|---|---|
| Foliage attitude. | More upright than the parent. | More relaxed when compared to 'OVPEARLS09'. |
| Foliage shape. | Narrow obovate to broad spathulate. | Obovate. |
| Foliage length. | Longer than the parent. | Shorter than 'OVPEARLS09'. |
| Foliar apex. | Cuspidate tip is longer than that of the parent. | Cuspidate tip is shorter than that of 'OVPEARLS09'. |
| Foliage thickness. | Thicker than the parent. | Thinner than 'OVPEARLS09'. |
| Undulation of the foliar margins. | Lightly undulated. | No undulation. |
| Presence of globular growths on the abaxial foliar surface. | Present. | None present. |

COMPARISONS WITH THE CLOSEST KNOWN COMPARATOR

Plants of the new cultivar 'OVPEARLS09' differ from *Echeveria lilacina* 'AMIECH2009' (U.S. patent application Ser. No. 17/300,674), which is the closest known comparator, in the following characteristics described in Table 2 below.

TABLE 2

| Characteristic | 'AMIECH2009' | 'OVPEARLS09' |
|---|---|---|
| Foliar margins. | Crenulate. | Entire. |
| Presence of globular growths on the abaxial foliar surface. | None present. | Present. |

TABLE 2-continued

| Characteristic | 'AMIECH2009' | 'OVPEARLS09' |
|---|---|---|
| General coloration of the mature foliage. | Pale greyed-green with a slight cyanic hue. | Pale greyed-green. |
| Distal portion of the leaf margins. | Narrowly margined with a translucent greyed-green. | Lightly margined with greyed-purple. |

That which is claimed is:

1. A new and distinct variety of *Echeveria* plant named 'OVPEARLS09', substantially as described and illustrated herein.

* * * * *